(12) United States Patent
Minami et al.

(10) Patent No.: US 8,137,733 B2
(45) Date of Patent: Mar. 20, 2012

(54) PROCESS FOR PRODUCING A CARRIER

(75) Inventors: Koichi Minami, Ashigarakami-gun (JP); Hirohiko Tsuzuki, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 659 days.

(21) Appl. No.: 12/276,004

(22) Filed: Nov. 21, 2008

(65) Prior Publication Data

US 2009/0140209 A1 Jun. 4, 2009

(30) Foreign Application Priority Data

Nov. 22, 2007 (JP) ................................. 2007-303028
Sep. 11, 2008 (JP) ................................. 2008-232839

(51) Int. Cl.
*G01N 1/31* (2006.01)
(52) U.S. Cl. ...................... 427/2.13; 252/408.1; 435/243
(58) Field of Classification Search .................. 427/2.13
See application file for complete search history.

(56) References Cited

U.S. PATENT DOCUMENTS 6,472,148 B1 * 10/2002 Bamdad et al. ................... 435/6

FOREIGN PATENT DOCUMENTS

| EP | 0497585 A | 8/1992 |
|---|---|---|
| JP | 06-157600 A | 6/1994 |
| JP | 2006-266831 A | 10/2006 |
| WO | 00/47548 A1 | 8/2000 |
| WO | 2006002472 A | 1/2006 |

OTHER PUBLICATIONS

European Patent Office Communication issued in corresponding European Patent Application No. 08 020 326.8, dated May 19, 2011.
Ueda, E., et al., "Current and prospective applications of metal ion-protein binding," J. of Chromatography, 988:1, Feb. 21, 2003, pp. 1-23.
Farid Khan et al., "Double-Hexahistidine Tag with High-Affinity Binding for Protein Immobilization, Purification, and Detection on Ni-Nitrilotriacetic Acid Surfaces", Analytical Chemistry, May 1, 2006, pp. 3072-3079, vol. 78, No. 9.
Suman Lata et al., "Stable and Functional Immobilization of Histidine-Tagged Proteins via Multivalent Chelator Headgroups on a Molecular Poly(ethylene glycol) Brush", Analytical Chemistry, Feb. 15, 2005, pp. 1096-1105, vol. 77, No. 4.
Mizuki Tada et al., "Molecular-Imprinted Supported Metal Complexes", Fine Chemical, 2007, pp. 33-41, vol. 36, No. 6.

* cited by examiner

*Primary Examiner* — Doris Lee
(74) *Attorney, Agent, or Firm* — Sughrue Mion, PLLC

(57) ABSTRACT

A complex, which has been formed by at least two pieces of a ligand and a first metal ion, is bound with a carrier. A second metal ion is then added onto the carrier, a new complex being thereby formed. A substance that contains a Group-15 or Group-16 atom, which has metal coordinating capability, is then fixed to the first metal ion and the second metal ion.

20 Claims, 2 Drawing Sheets

↓ ADDITION OF SECOND METAL ION

↓ ADDITION OF SUBSTANCE TO BE FIXED (SUBSTANCE THAT CONTAINS GROUP-15 or GROUP-16 ATOM, WHICH HAS METAL COORDINATING CAPABILITY)

PROCESS FOR PRODUCING A CARRIER

BACKGROUND OF THE INVENTION

1. Field of the Invention

This invention relates to a process for producing a carrier adapted for fixation of a substance that contains a Group-15 or Group-16 atom, which has a metal coordinating capability.

2. Description of the Related Art

Various analyses utilizing intermolecular interactions, such as immune reactions, have heretofore been performed in the fields of clinical examinations, and the like. Among others, several kinds of techniques, which do not require complicated operations and labeling substances and which are capable of detecting alterations in binding quantities of analyzed substances with a high sensitivity, have heretofore been used. Examples of the techniques described above include surface plasmon resonance (SPR) analysis techniques, quartz crystal oscillator microbalance (QCM) analysis techniques, and analysis techniques utilizing functional surfaces, such as surfaces of gold colloidal particles and ultrafine particles. In each of the techniques described above, a surface for fixation of a substance to be analyzed is important. By way of example, the surface plasmon resonance (SPR) analysis techniques will be described hereinbelow.

Ordinarily, an analysis chip for use in analysis of a substance to be analyzed is provided with a transparent carrier (e.g., a glass plate), a metal film, which has been formed on the transparent carrier by use of a vacuum evaporation processing, and a thin film, which has been formed on the metal film and which has a functional group capable of fixing a substance to be analyzed. The substance to be analyzed is fixed to the metal surface via the functional group. A specific binding reaction between the substance to be analyzed and a sample substance is analyzed, and an interaction between the substance to be analyzed and the sample substance is thereby analyzed.

Heretofore, there have been known several techniques for fixation of a substance that contains a Group-15 or Group-16 atom, which has a metal coordinating capability, to an analysis chip. For example, in cases where the substance that contains the Group-15 or Group-16 atom, which has the metal coordinating capability, is a protein, as a technique for fixing the analysis chip and the protein with each other through covalent bonding, there has been known a technique (i.e., an amine coupling technique), wherein an amino group of the protein and a carboxyl group on the analysis chip are bound with each other.

However, with the amine coupling technique, since an arbitrary amino group on the surface of the protein is modified due to the fixation, it often occurs that the orientation of fixed protein is not capable of coinciding with a predetermined orientation, or it often occurs that the binding of the protein and the substrate with each other is obstructed by the position of the modified amino group, and that the activity of the protein becomes low. Also, with the amine coupling technique, it is necessary for the protein to be concentrated on the analysis chip, and it is necessary that, at the time of the fixation, the protein is dissolved in a buffer solution, which has a pH value lower than pI of the protein to be fixed and which has a low ionic strength. Therefore, in the cases of a protein which undergoes denaturation under the conditions described above, the problems occur in that the fixation of the protein is not capable of being performed with the activity of the protein being kept.

Also, there have been developed techniques, wherein a protein is fixed onto an analysis chip under neutral conditions by use of a part referred to as a tag, which has been introduced to an N terminal or a C terminal of a protein having been synthesized artificially through generic alteration. A typical example of the technique described above is a fixation technique utilizing His-tag. The fixation technique utilizing the His-tag has been developed for an affinity column for purification of a His-tag protein having been expressed through genetic recombination. The fixation technique utilizing the His-tag has also been used for fixing a protein onto a solid surface such that the protein may have predetermined orientational characteristics.

Particularly, with a technique for fixation of the His-tag protein, wherein an NTA-Ni(II) complex having been formed from nitrilotriacetic acid (NTA) and an Ni(II) ion is utilized, water molecules having coordinated with two coordinating dentations in the complex are substituted by nitrogen atoms of two imidazole groups of an oligohistidine residue of the His-tag protein, and the His-tag protein is thereby bound with the solid surface specifically and in a predetermined direction. With the technique for fixation of the His-tag protein, wherein the NTA-Ni(II) complex is utilized, since pre-concentration under acidic conditions need not be performed, the fixation of the His-tag protein by use of a buffer solution (such as PBS) under physiological conditions is capable of being performed, and the problems encountered with the amine coupling technique are capable of being eliminated.

However, since the combination of the His-tag protein and the NTA-Ni(II) complex with each other has been developed for the purposes of the purification with the affinity column, the binding between the His-tag protein and the NTA-Ni(II) complex is not sufficiently strong, and the problems with regard to dissociation equilibrium are encountered. Therefore, the problems occur in that the His-tag protein having been fixed via the NTA-Ni(II) complex onto the analysis chip undergoes dissociation little by little from the analysis chip. Accordingly, the combination of the His-tag protein and the NTA-Ni(II) complex with each other is not capable of being applied directly to the use applications for biosensors, and the like.

Several studies have been made for solving the problems with regard to the dissociation described above. For example, fixation techniques, wherein substitution inactivation of a metal ion coordinating with the His-tag protein is effected through oxidation with an oxidizing agent, or the like, are disclosed in Japanese Unexamined Patent Publication Nos. 2006-266831 and 6(1994)-157600. However, with the disclosed fixation techniques, the problems often occur, depending upon the oxidation rate and the kind of the oxidizing agent, in that deactivation of the protein arises. Also, an attempt for improving the binding, wherein triNTA is utilized, in lieu of NTA described above, as a ligand and wherein the binding points of the His-tag protein is thereby increased (hereinbelow referred to as the multi-point binding), is described in, for example, International Patent Publication No. WO00/47548. However, with the attempt for improving the binding by the utilization of triNTA, it is not always possible to obtain practically sufficient fixation.

A technique for fixing NTA to a polysaccharide is disclosed in, for example, "Double-Hexahistidine Tag with High-Affinity Binding for Protein Immobilization, Purification, and Detection on Ni-Nitrilotriacetic Acid Surfaces", F. Khan et al., Anal. Chem., Vol. 78, No. 9, pp. 3072-3079, 2006. Also, a technique for fixation of the His-tag protein utilizing the NTA-Ni(II) complex, wherein the imidazole groups of the His-tag protein and NI(II) are bound at multiple points with the NTA ligand, is disclosed in, for example, "Stable and Functional Immobilization of Histidine-Tagged Proteins via Multivalent Chelator Headgroups on a Molecular Poly(ethylene glycol) Brush", S. Lata and J. Piehler, Anal. Chem., Vol. 77, No. 4, pp. 1096-1105, 2005. However, with the disclosed techniques, it is not always possible to form sufficiently strong binding.

Also, a technique, wherein a complex is formed previously and is bound with a surface and wherein thereafter a space optimum for a catalytic reaction is formed by a silica matrix, is disclosed in, for example, "Molecular-Imprinted Supported Metal Complexes", M. Tada and Y. Iwasawa, Fine Chemical, Vol. 36. pp. 33-41, 2007.

It may be presumed that, in cases where the substance that contains the Group-15 or Group-16 atom, which has the metal coordinating capability, is capable of being supported at multiple points, the binding force will be capable of being enhanced, and the aforesaid problems with regard to the dissociation will be capable of being solved. However, with the technique disclosed in "Double-Hexahistidine Tag with High-Affinity Binding for Protein Immobilization, Purification, and Detection on Ni-Nitrilotriacetic Acid Surfaces", F. Khan et al., Anal. Chem., Vol. 78, No. 9, pp. 3072-3079, 2006, wherein the fixation of the His-tag protein is performed with the length of His-tag being set to be long, since the adjacent NTA molecules are not close to each other, it is not always possible to support the His-tag protein easily at multiple points and to solve the problems with regard to the dissociation. Also, with the fixation technique disclosed in "Stable and Functional Immobilization of Histidine-Tagged Proteins via Multivalent Chelator Headgroups on a Molecular Poly (ethylene glycol) Brush", S. Lata and J. Piehler, Anal. Chem., Vol. 77, No. 4, pp. 1096-1105, 2005, since the ligands close to each other are rigid and are not capable of moving flexibly, the problems are encountered in that the metal is not always capable of coordinating at multiple points with the substance that contains the Group-15 or Group-16 atom, which has the metal coordinating capability, and in that actually it is not always possible to fix the substance that contains the Group-15 or Group-16 atom, which has the metal coordinating capability, reliably at multiple points.

Further, in "Molecular-Imprinted Supported Metal Complexes", M. Tada and Y. Iwasawa, Fine Chemical, Vol. 36. pp. 33-41, 2007, it is described that a space having the same shape as the shape of a template molecule is formed within a matrix by polymerization or lamination of an organic polymer or an inorganic matrix. However, with the fixation technique disclosed in the monthly publication, the problems are encountered with regard to insufficiency of washing of the template molecule from the space and lowering of a template molecule fetching rate by matrix formation. Furthermore, the problems are encountered in that the template molecule is not capable of being fixed reliably due to deformation of the template molecule at the time of the matrix forming reaction. Also, the problems are encountered with regard to lowering of reproducibility due to softness of the matrix. Further, the problems are encountered in that, in the cases of a hard substance, the fixation technique is not capable of being applied to a catalytic reaction, an antigen-antibody reaction, or the like, which accompanies a dynamic alteration of the molecular shape.

SUMMARY OF THE INVENTION

The primary object of the present invention is to provide a process for producing a carrier, which reliably fixes a substance that contains a Group-15 or Group-16 atom having metal coordinating capability.

The present invention provides a process for producing a carrier, comprising the steps of:

(1) binding a complex, which has been formed by at least two pieces of a ligand and a first metal ion, with a carrier, (2) adding a second metal ion onto the carrier, a new complex being thereby formed, and (3) fixing a substance that contains a Group-15 or Group-16 atom, which has metal coordinating capability, to the first metal ion and the second metal ion, the steps (1), (2), and (3) being performed in this order.

The process for producing a carrier in accordance with the present invention should preferably be modified such that a quantity of the second metal ion added in the step (2) is set at a value which cleaves approximately all of the complex having been bound to the carrier in the step (1).

Also, the process for producing a carrier in accordance with the present invention should preferably be modified such that the ligand is a nitrilotriacetic acid derivative.

Further, the process for producing a carrier in accordance with the present invention should preferably be modified such that the first metal ion, which is employed in the step (1), and/or the second metal ion, which is employed in the step (2), is a transition metal ion. Furthermore, the process for producing a carrier in accordance with the present invention should more preferably be modified such that the transition metal ion, which is employed in the step (2), is selected from the group consisting of a nickel ion, a copper ion, and a cobalt ion.

Also, the process for producing a carrier in accordance with the present invention should preferably be modified such that the substance that contains the Group-15 or Group-16 atom is a substance having at least two heterocyclic rings each of which contains the Group-15 or Group-16 atom. Further, the process for producing a carrier in accordance with the present invention should more preferably be modified such that the substance having at least two heterocyclic rings is a physiologically active substance having at least two heterocyclic rings each of which contains the Group-15 or Group-16 atom.

Furthermore, the process for producing a carrier in accordance with the present invention should more preferably be modified such that the physiologically active substance is a physiologically active substance having at least two imidazole groups.

Also, the process for producing a carrier in accordance with the present invention should preferably be modified such that a fixation quantity of the complex having been bound with the carrier in the step (1) falls within the range of $1 \times 10^{-12}$ g/mm$^3$ to $1 \times 10^{-3}$ g/mm$^3$.

The carrier produced by the process in accordance with the present invention is utilized appropriately as a carrier for a bioreactor or a biosensor. The carrier produced by the process in accordance with the present invention is utilized more appropriately for surface plasmon resonance analysis.

With the process for producing a carrier in accordance with the present invention, the complex, which has been formed by at least two pieces of the ligand and the first metal ion, is bound with the carrier, and the second metal ion is added onto the carrier, the new complex being thereby formed. Therefore, the plurality of pieces of the ligand are located close to one another and are fixed to the carrier surface. Accordingly, the substance that contains the Group-15 or Group-16 atom, which has the metal coordinating capability, is fixed at multiple points to the plurality of pieces of the ligand via the first metal ion and the second metal ion. The substance that contains the Group-15 or Group-16 atom, which has the metal coordinating capability, is thus fixed reliably.

The present invention will hereinbelow be described in further detail with reference to the accompanying drawings.

DETAILED DESCRIPTION OF THE INVENTION

Figure 1A:
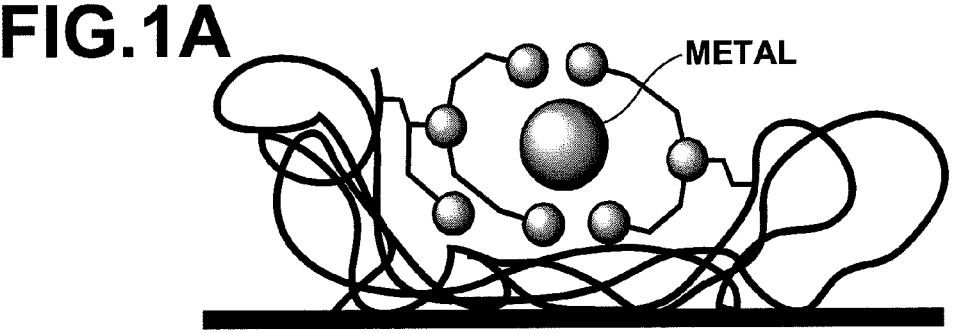
FIGS. 1A, 1B, and 1C are explanatory views showing how a carrier is produced by the process for producing a carrier in accordance with the present invention.

The process for producing a carrier in accordance with the present invention comprises the steps of:

(1) binding the complex, which has been formed by at least two pieces of the ligand and the first metal ion, with the carrier, (2) adding the second metal ion onto the carrier, the new complex being thereby formed, and (3) fixing the substance that contains the Group-15 or Group-16 atom, which has the metal coordinating capability, to the first metal ion and the second metal ion, the steps (1), (2), and (3) being performed in this order.

The steps (1), (2), and (3) in the process for producing a carrier in accordance with the present invention will be described hereinbelow with reference to FIGS. 1A, 1B, and 1C.

(1) The Step of Binding the Complex, which has been Formed by at Least Two Pieces of the Ligand and the First Metal Ion, With the Carrier (1-1) Carrier The carrier employed in the present invention may be constituted of one of various materials, e.g., glass; silica; metal oxides, such as alumina, titania, zirconia, and indium tin oxide (ITO); metal nitrides, such as silicon nitride, gallium nitride, aluminum nitride, and indium nitride; and synthetic resins, such as a sepharose, a polyethylene, a polystyrene, a poly(meth)acrylic acid, a poly(meth)acrylamide, a polymethyl(meth)acrylate, a polyethylene terephthalate, a polycarbonate, and a cycloolefin polymer. The above-enumerated materials for the carrier should preferably be imparted with a functional group. Examples of the functional groups include an amino group, a carboxyl group, a maleimido group, an aldehyde group, a succinimido group, a thiol group, a hydrazine group, an isocyanate group, an epoxy group, a vinyl sulfone group, a vinyl group, and a cyano group.

As a technique for imparting the functional groups described above, it is possible to employ one of various known surface processing techniques, such as plasma processing, ozone processing, acid or alkali etching processing, and self-assembled monolayer processing. The self-assembled monolayer processing should preferably be employed.

Examples of the techniques for forming the self-assembled monolayer include <1> a technique using a silane coupling agent, and <2> a technique using an alkanethiol.

<1> Technique Using a Silane Coupling Agent

With the technique using the silane coupling agent, the silane coupling agent described below is imparted to the carrier described above. As a result, the self-assembled monolayer with the silane coupling agent is formed, and the functional group is imparted onto the carrier.

In the process for producing a carrier in accordance with the present invention, as the silane coupling agent, it is possible to use a silicon-containing compound that is represented by the general formula A-1 shown below, wherein $X^a$ represents a functional group, $L^a$ represents a linker moiety containing a straight, branched, or cyclic carbon chain, $R^a$ represents hydrogen or an alkyl group having one to six carbon atoms, $Y^a$ represents a hydrolyzable group, and each of m and n represents an integral number falling within the range of 0 to 3, with the proviso that m+n=3. A covalent bond expressed as carrier-oxygen-silicon-carbon is thus formed, and the functional group is imparted to the carrier surface.

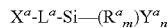

$$X^a\text{-}L^a\text{-Si---}(R^a_m)Y^a_n \qquad \text{A-1}$$

Examples of the hydrolyzable groups ($Y^a$) include an alkoxy group, a halogen, and an acyloxy group. Specifically, examples of the hydrolyzable groups ($Y^a$) include a methoxy group, an ethoxy group, and chlorine. Examples of the silane coupling agents include γ-aminopropyltrimethoxysilane, N-β(aminoethyl) γ-aminopropyltrimethoxysilane, γ-aminopropylmethyldiethoxysilane, γ-mercaptopropyltrimethoxysilane, and γ-glycidoxypropyltriethoxysilane. The reaction of the silane coupling agent may be performed in accordance with an ordinary procedure, e.g. the procedure described in a book "Effects and Usage of Silane Coupling Agents" (published by Science & Technology Co.).

The functional group ($X^a$) which the silane coupling agent has may be selected from a wide variety of functional groups, which bind with polymers and complexes described later. As the functional group ($X^a$), it is possible to utilize an arbitrary functional group, such as an amino group, a carboxyl group, a hydroxyl group, an aldehyde group, a thiol group, an isocyanate group, an isothiocyanate group, an epoxy group, a cyano group, a hydrazino group, a hydrazide group, a vinyl sulfone group, a vinyl group, a maleimido group, a combination of two or more of the above-enumerated functional groups, and derivatives of the above-enumerated functional groups. The functional group ($X^a$) should preferably be the amino group or the epoxy group.

<2> Technique Using an Alkanethiol

With the technique using the alkanethiol, a metal film is located on the aforesaid carrier, and thereafter the alkanethiol is imparted. The term "located on a carrier" as used herein embraces the cases wherein the metal film is located on the carrier so as to be in direct contact with the carrier, and the cases wherein, instead of being in direct contact with the carrier, the metal film is located on the carrier via a different layer. By way of example, in cases where the carrier is to be applied to the surface plasmon resonance biosensor, the metal for constituting the metal film may be selected from a wide variety of metals, which enable the occurrence of the surface plasmon resonance. The metal for constituting the metal film should preferably be selected from free electron metals, such as gold, silver, copper, aluminum, and platinum, and should more preferably be gold. Each of the above-enumerated metals may be used alone, or at least two kinds of metals among the above-enumerated metals may be used in combination. Also, with adhesion characteristics with respect to the carrier being taken into consideration, an intervening layer constituted of chromium, or the like, may be located between the carrier and the layer constituted of the metal.

The film thickness of the metal film may be set at an arbitrary value. By way of example, in cases where the carrier is to be applied to the surface plasmon resonance biosensor, the film thickness of the metal film should preferably fall within the range of 0.1 nm to 500 nm, and should more preferably fall within the range of 1 nm to 200 nm. If the film thickness of the metal film is larger than 500 nm, the surface plasmon phenomenon of the medium will not be capable of being detected sufficiently. In cases where the intervening layer constituted of chromium, or the like, is located between the carrier and the metal film, the thickness of the intervening layer should preferably fall within the range of 0.1 nm to 10 nm.

A technique for covering a metal film by use of the alkanethiol has been developed vigorously by Professor Whitesides of Harvard University, et al. The details of the technique for covering a metal film by use of self-assembled monolayers have been reported in, for example, Chemical Review, 105, 1103-1169 (2005). In cases where gold is employed as the metal, an alkanethiol, which may be represented by the general formula A-2 shown below, wherein n represents an integral number falling within the range of 3 to 20 and wherein $X^b$ represents a functional group, may be used as the organic layer forming compound. In such cases, a monolayer having orientational characteristics is formed in a self-assembled manner in accordance with van der Waals force of the Au—S bond and the alkyl group with each other. The self-assembled monolayer is prepared with a markedly simple technique, wherein the gold carrier is dipped in a solution of the alkanethiol derivative. Specifically, for example, the self-assembled monolayer may be formed by use of the compound, which may be represented by the general formula A-2, wherein $X^b$ represents an amino group, a carboxyl group, a hydroxyl group, an aldehyde group, a thiol group, an isocyanate group, an isothiocyanate group, an epoxy group, a cyano group, a hydrazino group, a hydrazide group, a vinyl sulfone group, a vinyl group, or a maleimido group. The functional group is thus capable of being imparted to the carrier surface.

$$HS(CH_2)_nX^b \qquad\qquad A\text{-}2$$

In the general formula A-2, the repetition number (n) of the alkyl group should preferably be an integral number falling within the range of 3 to 16, and should more preferably be an integral number falling within the range of 4 to 8. Also, the alkyl group moiety may be substituted by a multiple bond or a heteroatom, such as nitrogen or oxygen. If the alkyl chain of the alkanethiol derivative is markedly short, the self-assembled monolayer will not always be capable of being formed. If the alkyl chain of the alkanethiol derivative is markedly long, the solubility in water will become low, and handling characteristics will become bad.

Further, the self-assembled monolayer is capable of being formed by use of the alkanethiol, which may be represented by the general formula A-2, wherein the functional group $X^b$ represents only one kind of the functional group. Furthermore, the self-assembled monolayer is capable of being formed by use of a mixture of the alkanethiol, which may be represented by the general formula A-2, and other kinds of alkanethiols.

Also, in the process for producing a carrier in accordance with the present invention, a polymer may be coated on the self-assembled monolayer having been formed, and the functional group may thus be imparted to the carrier surface. In such cases, as the polymer, a hydrophilic polymer should preferably be used. Examples of the hydrophilic polymers, which may be employed in the present invention, include gelatin, agarose, chitosan, dextran, carrageenan, alginic acid, starch, cellulose, and derivatives of the above-enumerated hydrophilic polymers, such as carboxymethyl derivatives; and water-swelling organic polymers, such as a polyvinyl alcohol, a polyacrylic acid, a polyacrylamide, a polyethylene glycol, and derivatives of the above-enumerated water-swelling organic polymers.

As the hydrophilic polymer, which may be employed in the present invention, it is also possible to use a carboxyl group-containing synthetic polymer or a carboxyl group-containing polysaccharide. Examples of the carboxyl group-containing synthetic polymers include a polyacrylic acid, a polymethacrylic acid, and copolymers thereof, e.g. copolymers as described in Japanese Unexamined Patent Publication No. 59(1984)-53836, page 3, line 20 to page 6, line 49, and Japanese Unexamined Patent Publication No. 59(1984)-71048, page 3, line 41 to page 7, line 54, such as a methacrylic acid copolymer, an acrylic acid copolymer, an itaconic acid copolymer, a crotonic acid copolymer, a maleic acid copolymer, a partially esterified maleic acid copolymer, and an addition product of a polymer having a hydroxyl group and an acid anhydride. The carboxyl group-containing polysaccharide may be an extract from a natural plant, a product of microorganism fermentation, a synthetic product obtained with an enzyme, or a chemical synthetic product. Examples of the carboxyl group-containing polysaccharides include hyaluronic acid, chondroitin sulfate, heparin, dermatan sulfate, carboxymethyl cellulose, carboxyethyl cellulose, cellouronic acid, carboxymethyl chitin, carboxymethyl dextran, and carboxymethyl starch. As the carboxyl group-containing polysaccharide, it is possible to use a commercially available compound. Examples of the commercially available compounds include CMD (carboxymethyl dextran), CMD-L, and CMD-D40 (which are supplied by Meito Sangyo Co., Ltd.); sodium carboxymethyl cellulose (which is supplied by Wako Pure Chemical Industries, Ltd.); and sodium alginate (which is supplied by Wako Pure Chemical Industries, Ltd.).

No limitation is imposed upon a molecular weight of the hydrophilic polymer employed in the present invention. Ordinarily, the molecular weight of the hydrophilic polymer employed in the present invention should preferably fall within the range of 200 to 5,000,000, and should more preferably fall within the range of 10,000 to 2,000,000.

As for the hydrophilic polymer, the film thickness of the hydrophilic polymer in an aqueous solution should preferably fall within the range of 0.5 nm to 0.5 mm, and should more preferably fall within the range of 1 nm to 1 μm. If the film thickness is markedly small, the fixation quantity of the physiologically active substance will become small, and the interaction with the sample substance will not be always capable of occurring. If the film thickness is markedly large, there will be the risk that the uniformity of the hydrophilic polymer is not kept. The film thickness of the hydrophilic polymer in the aqueous solution is capable of being evaluated with AFM, ellipsometry, or the like.

In cases where the polymer containing the carboxyl group is used, with a technique for activating the carboxyl group, the polymer is capable of being fixed to the carrier via the functional group having been imparted to the carrier surface. As the technique for activating the polymer containing the carboxyl group, it is possible to use appropriately a known technique, e.g., a technique for activating with 1-(3-dimethylaminopropyl)-3-ethylcarbodiimide (EDC), which is a water-soluble carbodiimide, and N-hydroxysuccinimide (NHS), or a technique for activating with EDC alone. In cases where the polymer containing the carboxyl group, which polymer has been activated with the technique described above, is caused to react with the carrier having the amino group, the hydrophilic polymer is capable of being bound on the carrier.

Also, as the technique for activating the polymer containing the carboxyl group, it is possible to use a technique wherein a nitrogen-containing compound is utilized. Specifically, it is possible to utilize a nitrogen-containing compound represented by the general formula (Ia) or the general formula (Ib) shown below, wherein each of $R^1$ and $R^2$ independently represents a carbonyl group, a carbon atom, or a nitrogen atom, which may have a substituent group, or $R^1$ and $R^2$ jointly represent a five-membered ring or a six-membered ring, A represents a carbon atom or a phosphorus atom, which has a substituent group, M represents an (n-1)-valent element, and X represents a halogen atom.

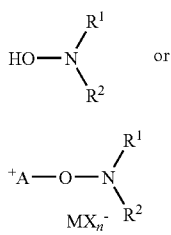 (Ia)

(Ib)

In this case, each of $R^1$ and $R^2$ may independently represent a carbonyl group, a carbon atom, or a nitrogen atom, which may have a substituent group. Preferably, $R^1$ and $R^2$ jointly represent the five-membered ring or the six-membered ring. Particularly preferably, there is furnished hydroxysuccinic acid, hydroxyphthalic acid, 1-hydroxybenzotriazole, 3,4-dihydroxy-3-hydroxy-4-oxo-1,2,3-benzotriazine, and derivatives of the above-enumerated compounds.

It is also possible to utilize preferably the nitrogen-containing compounds, which may be represented by the formulas shown below.

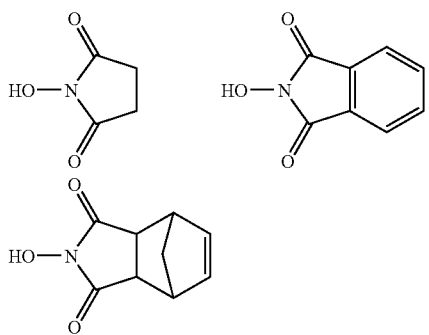

Further, as the nitrogen-containing compound, it is possible to utilize preferably the compound, which may be represented by the general formula (I) shown below, wherein each of Y and Z independently represents CH or a nitrogen atom.

General formula (I)

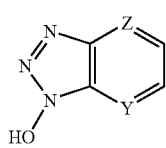

Preferable examples of the compounds, which may be represented by the general formula (I), include the compounds, which may be represented by the formulas shown below.

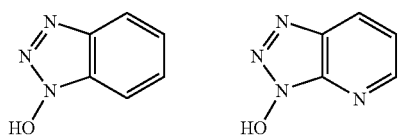

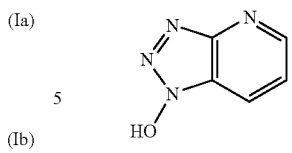

Furthermore, as the nitrogen-containing compound, it is possible to utilize preferably the compound, which may be represented by the formula shown below.

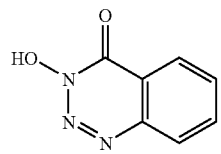

Also, as the nitrogen-containing compound, it is possible to utilize preferably the compound, which may be represented by the general formula (II) shown below, wherein A represents a carbon atom or a phosphorus atom, which has a substituent group, each of Y and Z independently represents CH or a nitrogen atom, M represents an (n-1)-valent element, and X represents a halogen atom.

General formula (II)

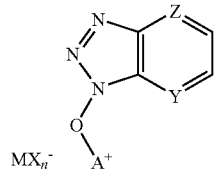

In this case, the substituent group, which the carbon atom or the phosphorus atom has, should preferably be an amino group having a substituent group, and should more preferably be a dialkylamino group, such as a dimethylamino group, or a pyrrolidino group. The (n-1)-valent element, which is represented by M, may be, for example, a phosphorus atom, a boron atom, or an arsenic atom, and should preferably be the phosphorus atom. The halogen atom, which is represented by X, may be a fluorine atom, a chlorine atom, a bromine atom, or an iodine atom, and should preferably be the fluorine atom.

Preferable examples of the compounds, which may be represented by the general formula (II), include the compounds, which may be represented by the formulas shown below.

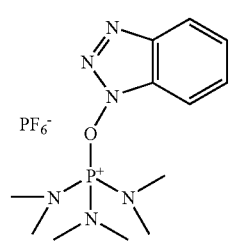 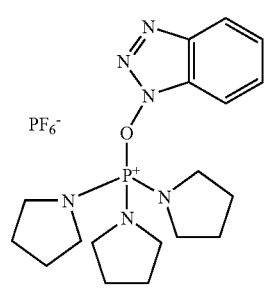

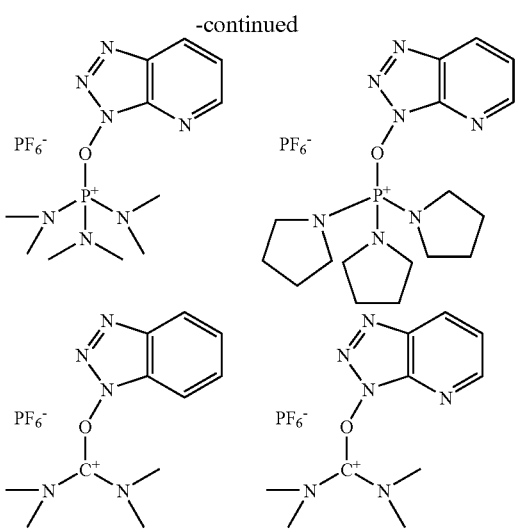

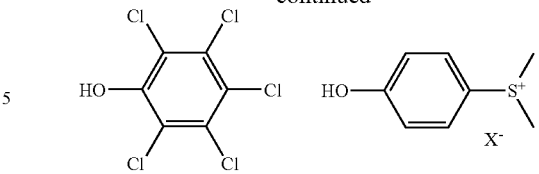

Further, as the nitrogen-containing compound, it is possible to utilize preferably the compound, which may be represented by the general formula (III) shown below, wherein A represents a carbon atom or a phosphorus atom, which has a substituent group, M represents an (n-1)-valent element, and X represents a halogen atom.

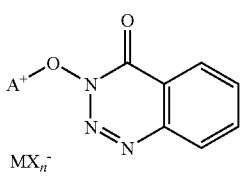

General formula (III)

A preferable example of the compound, which may be represented by the general formula (III), is the compound, which may be represented by the formula shown below.

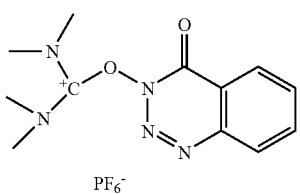

Further, as the technique for activating the polymer containing the carboxyl group, it is possible to use preferably a technique wherein a phenol derivative, which has an electron-attracting group, is utilized. In such cases, the electron-attracting group should preferably have the σ value of at least 0.3. Specifically, it is possible to utilize, for example, the compounds, which may be represented by the formulas shown below.

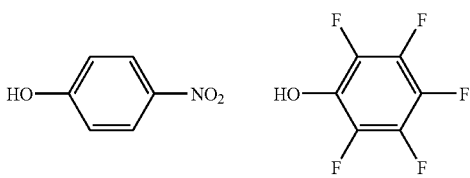

The carbodiimide derivative described above may be utilized in combination with the nitrogen-containing compound or the phenol derivative. Alternatively, when necessary, each of the carbodiimide derivative described above, the nitrogen-containing compound, and the phenol derivative may be utilized alone. There should preferably be utilized the combination of the carbodiimide derivative and the nitrogen-containing compound.

Also, as the technique for activating the polymer containing the carboxyl group, it is possible to use a technique wherein the compound, which may be represented by the formula shown below, is utilized. The compound, which may be represented by the formula shown below, may be utilized alone or in combination with the carbodiimide derivative, the nitrogen-containing compound, and/or the phenol derivative.

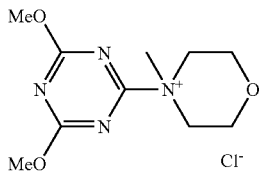

Further, as the technique for activating carboxylic acid in the polymer containing the carboxyl group, it is possible to use preferably a technique described in Japanese Unexamined Patent Publication No. 2006-58071, [0011] to [0022] (i.e., the technique, wherein a carboxyl group located on a surface of a carrier is activated by use of a compound selected from the group consisting of a uronium salt, a phosphonium salt, and a triazine derivative, which have specific structures, and wherein a carboxylic acid amido group is thereby formed). It is also possible to use preferably a technique described in Japanese Unexamined Patent Publication No. 2006-90781, [0011] to [0019] (i.e., the technique, wherein a carboxyl group located on a surface of a carrier is activated by use of a carbodiimide derivative or a salt thereof, wherein esterification is performed by use of a compound selected from the group consisting of a nitrogen-containing heteroaromatic compound having a hydroxyl group, a phenol derivative having an electron-attracting group, and an aromatic compound having a thiol group, wherein a reaction with an amine is performed, and wherein a carboxylic acid amido group is thereby formed).

In the present invention, the polymer containing the carboxyl group having been activated may be caused to undergo the reaction with the carrier in the form of a solution. Alternatively, the polymer containing the carboxyl group having been activated may be applied to form a thin film on the carrier by use of a technique, such as a spin coating technique, and may be caused to undergo the reaction with the carrier in the state of the thin film. The polymer should preferably be caused to undergo the reaction with the carrier in the state of the thin film.

As described above, in the present invention, the polymer containing the carboxyl group having been activated should preferably be caused to undergo the reaction with the carrier in the state of the thin film. As the technique for forming the thin film on carrier, one of known techniques may be employed. Specifically, it is possible to employ an extrusion coating technique, a curtain coating technique, a casting technique, a screen printing technique, a spin coating technique, a spray coating technique, a slide beads coating technique, a slit and spin technique, a slit coating technique, a die coating technique, a dip coating technique, a knife coating technique, a blade coating technique, a flow coating technique, a roll coating technique, a wire bar boating technique, a transfer printing technique, or the like. The thin film forming techniques are described in, for example, "Coating Gijutsu No Shinpo" (Progress of Coating Technology), written by Yuji Harasaki, Sogo Gijutsu Center (1988); "Coating Gijutsu" (Coating Technology), Technical Information institute Co., Ltd. (1999); "Suisei Coating No Gijutsu" (Aqueous Coating Technology), CMC (2001); "Shinka Suru Yuki Hakumaku Seimaku-Hen" (Evolving Organic Thin Film, Film Formation Edition), Sumibe Techno Research Co., Ltd. (2004); and "Kobunshi Hyomen Kako Gaku" (Polymer Surface Processing Engineering), written by Akatsuki Iwamori, Gihodo Shuppan (2005). In the present invention, as the technique for forming the thin film on the carrier, the spray coating technique or the spin coating technique should preferably be employed, and the spin coating technique should more preferably be employed. With the spray coating technique or the spin coating technique, a coating film having a controlled film thickness is capable of being prepared easily.

In the present invention, by use of one of the techniques described above, the complex is bound on the carrier having been imparted with the functional group.

(1-2) Ligand

As the compound acting as the ligand, it is possible to employ various kinds of chelating agents. Preferable examples of the ligands include multidentate ligands, such as nitrilotriacetic acid (NTA), iminodiacetic acid (IDA), phenanthroline, terpyridine, bipyridine, triethylenetetramine, bi(ethylenetriamine), tris(carboxymethyl)ethylenediamine, diethylenetriaminepentaacetic acid, polypyrazolylboric acid, 1,4,7-triazocyclononane, dimethylglyoxime, diphenylglyoxime, and derivatives of the above-enumerated compounds. The term "derivative" as used herein means the compound having been modified with a functional group, which is capable of binding with the functional group having been imparted onto the carrier.

(1-3) First Metal Ion

The first metal ion may be selected from various kinds of metal ions capable of forming metal complexes. From the view point of the stability of the metal complex obtained, the first metal ion should preferably be a transition metal ion. Preferable examples of the first metal ions include Ni(II), Cu(I), Cu(II), Co(II), Co(III), Fe(II), Fe(III), Ga(III), Ru(III), Ag(I), Au(III), V(V), Zn(II), Mn(II), Mn(III), Zr(IV), Hf(IV), and In(III). The first metal ion may be selected appropriately in accordance with the kind of the ligand.

The metal ion varies in binding force in accordance with the valence number. In the cases of Co(II) or Fe(II), the binding force of the metal ion is capable of being altered through an alteration of the oxidation number of the metal ion by use of an oxidation-reduction technique as described in, for example, Japanese Unexamined Patent Publication No. 6(1994)-157600, [0037] and [0038].

(1-4) Formation of the Complex and the Technique for Binding the Complex with the Carrier (FIG. 1A)

In the present invention, the complex formed by at least two pieces of the ligand and the first metal ion may be formed by use of a known technique. The complex is capable of being obtained by processing, wherein the ligand described under (1-2) and the first metal ion described under (1-3) are mixed together. For example, the complex having at least two pieces of the ligand is obtained by the processing, wherein a nitrilotriacetic acid derivative acting as the ligand, ethylenediamine acting as the ligand, and copper chloride are mixed together in a molar ratio of 1:1:1 in an aqueous solution. In such cases, the at least two pieces of the ligand may be the same kind of the ligand. Alternatively, different kinds of ligands may be employed as the at least two pieces of the ligand. The ligand may be added in a quantity such that at least two pieces of the ligand coordinate with respect to the coordination number which the metal ion has. From the view point of the control of the number of the formed complex species, the number of pieces of the ligand coordinating with the metal should preferably be two or three.

The metal complex having been formed with the technique described above may be subjected to a reaction and binding appropriately in accordance with the kind of the functional group having been imparted to the carrier. The binding technique may be selected from the binding techniques known in the art. For example, it is possible to employ the technique, wherein the carboxyl group is activated by EDC, or the like, described above and is bound with the amino group, or the technique, wherein the binding is performed by the maleimido group-thiol group reaction. However, the present invention is not limited to the binding techniques described above. In cases where the carrier produced with the process in accordance with the present invention is to be used for the biosensor utilizing the surface plasmon resonance, the fixation quantity of the complex having been bound with the carrier should preferably fall within the range of $1 \times 10^{-12}$ g/mm$^3$ to $1 \times 10^{-3}$ g/mm$^3$. In such cases, the fixation quantity of the complex having been bound with the carrier should more preferably fall within the range of $1 \times 10^{-11}$ g/mm$^3$ to $1 \times 10^{-5}$ g/mm$^3$, and should most preferably fall within the range of $1 \times 10^{-9}$ g/mm$^3$ to $1 \times 10^{-5}$ g/mm$^3$. In cases where the carrier produced with the process in accordance with the present invention is to be used for the biosensor utilizing a fluorescent label, the fixation quantity of the complex having been bound with the carrier is not limited to the range described above, and sufficient effects are obtained with the fixation quantity of the complex falling within the range of $1 \times 10^{-21}$ g/mm$^3$ to $1 \times 10^{-3}$ g/mm$^3$.

The volume density described above is capable of being found in the manner described below. Specifically, in cases where the volume density is to be found with a measurement being made actually, after the complex has been bound on the support, the number of pieces of the metal ion having been fixed on the support is calculated by use of an ICP analysis apparatus, or the like, and the number of pieces of the complex per unit volume is found in accordance with the volume of the region of the support, at which region the complex has been bound. In cases where the volume density is to be found with a calculation, the volume of the complex may be found by use of a calculation software function, such as CHEM 3 D (supplied by CambridgeSoft), and the number of pieces of the complex per unit volume may thereby be calculated. In cases where the volume of the complex is found by use of the calculation software function, e.g. as for the NTA complex, the volume is estimated to be approximately 0.3 nm$^3$.

Figure 1B:
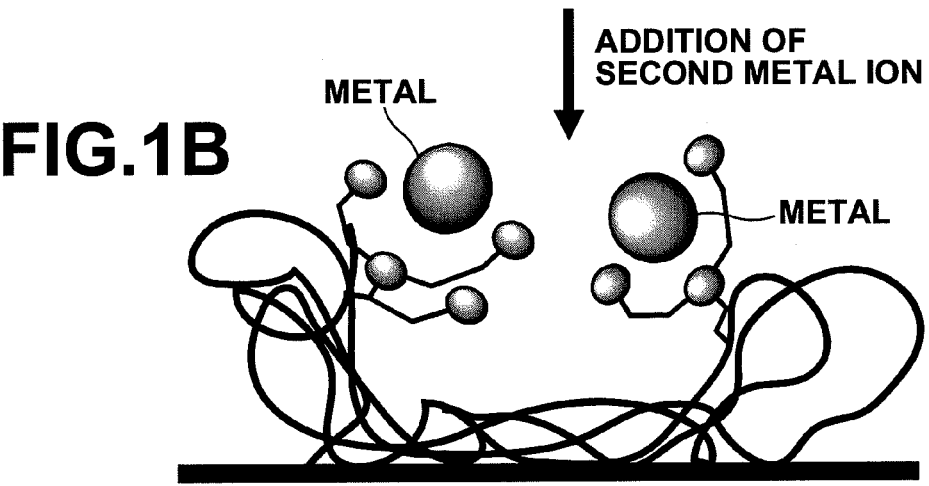

(2) The Step of Adding the Second Metal Ion onto the Carrier, the New Complex being Thereby Formed (FIG. 1B)

In this step, the second metal ion is added onto the carrier, and the new complex is thereby formed. The quantity of the second metal ion added in this step should preferably be set at a value which cleaves approximately all of the complex having been bound to the carrier in the step described under (1). The term "value which cleaves approximately all of a complex having been bound to a carrier in a step described under (1)" as used herein means the quantity which cleaves at least 80% of the complex having been bound to the carrier in the step described under (1), and preferably the quantity which cleaves at least 90% of the complex having been bound to the carrier in the step described under (1).

As illustrated in FIG. 1B, in cases where the second metal ion is added onto the carrier, the complex having been fixed to the carrier surface is cleaved, and the plurality of pieces of the metal ions are located close to one another (close chelate modification). Therefore, as will be described later, it is considered that the substance that contains the Group-15 or Group-16 atom, which has the metal coordinating capability, is fixed at multiple points. (The term "fixed at multiple points" as used herein means that the ligand and the substance that contains the Group-15 or Group-16 atom are bound with a plurality of pieces of the metal ions. The second metal ion added in this step may be of the same kind as the kind of the first metal ion used in the step described under (1). Alternatively, the second metal ion added in this step may be of the kind different from the kind of the first metal ion used in the step described under (1). The second metal ion added in this step described under (2) should preferably be a transition metal ion, such as Ni (II), Cu(I), Cu(II), Co(II), Co(III), Fe(II), Fe(III), Ga(III), or Ru(III). The second metal ion added in this step described under (2) should more preferably be a nickel ion (Ni(II)), a copper ion (Cu(II)), a cobalt ion (Co(II)), or a cobalt ion (Co(III)).

In this step, the second metal ion may be added in a large quantity. However, from the view point of suppression of the metal ion adsorbed to the carrier, or the like, in a non-specific manner due to the addition of the large quantity of the second metal ion, the quantity of the second metal ion added in this step should preferably fall within the range of $6.02 \times 10^{10}$ pieces/mm$^3$ to $6.02 \times 10^{21}$ pieces/mm$^3$.

(3) The Step of Fixing the Substance that Contains the Group-15 or Group-16 Atom, which has the Metal Coordinating Capability, to the First Metal Ion and the Second Metal Ion (3-1) Substance that Contains the Group-15 or Group-16 Atom, which has the Metal Coordinating Capability In the present invention, the substance that contains the Group-15 atom (N, P, As, Sb, or Bi) or the Group-16 atom (O, S, Se, Te, or Po), which has the metal coordinating capability, may be, for example, a substance having at least two heterocyclic rings each of which contains the Group-15 or Group-16 atom. Alternatively, the substance that contains the Group-15 or Group-16 atom may be a phosphine compound or a selenium compound. The substance that contains the Group-15 or Group-16 atom should preferably be the substance having at least two heterocyclic rings each of which contains the Group-15 or Group-16 atom. For example, the heterocyclic rings each of which contains the Group-15 or Group-16 atom may be a nitrogen-containing heterocyclic ring.

The nitrogen-containing heterocyclic ring may have a monocyclic structure or a condensed ring structure, which contains a three- to seven-membered ring containing the nitrogen atom. The number of the nitrogen atom contained in the ring may be at least one. The nitrogen-containing heterocyclic ring should preferably contain a five-membered ring or a six-membered ring. Examples of the ligands having the nitrogen-containing heterocyclic rings include pyrrole, imidazole, pyrazole, oxazole, isoxazole, thiazole, isothiazole, 1,2,3-triazole, 1,2,4-triazole, 1,3,4-thiadiazole, tetrazole, pyridine, pyrazine, pyrimidine, pyridazine, 1,2,3-triazine, 1,2,4-triazine, 1,3,5-triazine, 1,2,4,5-tetrazine, azepine, azonine, quinoline, acridine, phenanthridine, indole, isoindole, carbazole, benzimidazole, 1,8-naphthyridine, purine, pteridine, benzotriazole, quinoxaline, quinazoline, perimidine, cinnoline, phthalazine, 1,10-phenanthroline, phenoxazine, phenothiazine, phenazine, 8-hydroxyquinoline, 8-mercaptoquinoline, 2,2'-bipyridine, 2,2'-dipyridylamine, di(2-picolylamine), 2,2',2''-terpyridine, porphyrine, phthalocyanine, and derivatives of the above-enumerated compounds. From the view point of the stability of the metal complex obtained, the ligand having the nitrogen-containing heterocyclic ring should preferably be pyrrole, imidazole, pyrazole, oxazole, thiazole, pyridine, or a derivative of one of the above-enumerated compounds.

The Group-15 or Group-16 atom, which has the metal coordinating capability, is capable of being imparted easily through covalent bonding or in a manner of genetic engineering in the cases of a physiologically active substance. Examples of the physiologically active substances include an immune protein, an enzyme, a microorganism, nucleic acid, a low molecular weight organic compound, a non-immune protein, an immune globulin binding protein, a saccharide binding protein, a saccharide-recognizing saccharide chain, fatty acid or a fatty acid ester, and a polypeptide or an oligopeptide, which has ligand binding capability. For the advantages in that the introduction by use of an amino acid automatic synthesizing apparatus or the introduction by genetic engineering is easy, the physiologically active substance should preferably have the imidazole group.

Figure 1C:
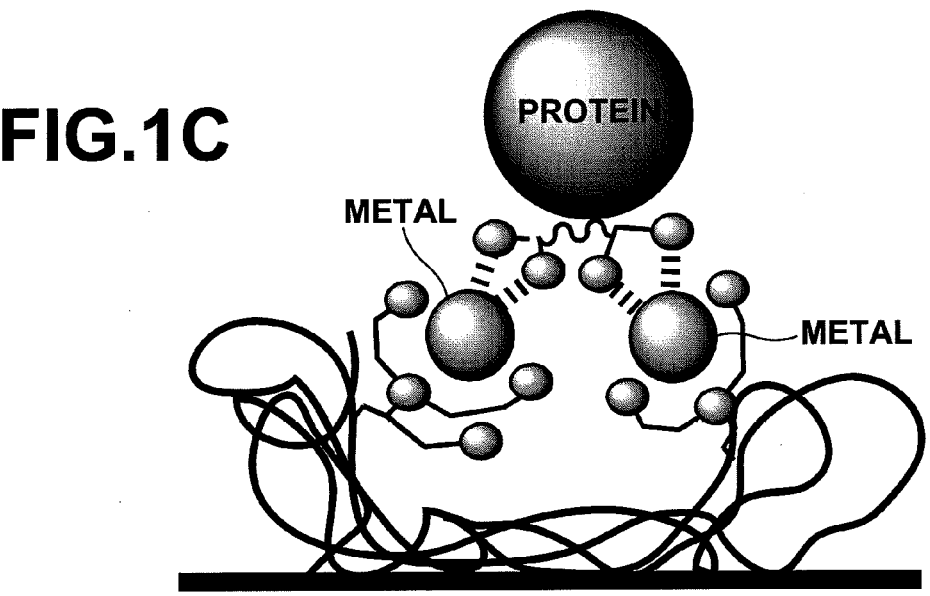

(3-2) Fixation of the Substance that Contains the Group-15 or Group-16 Atom (FIG. 1C)

The fixation of the substance that contains the Group-15 or Group-16 atom, which has the metal coordinating capability, may be performed with processing for coating a solution or a solid containing the substance that contains the Group-15 or Group-16 atom, which has the metal coordinating capability, on the surface of the carrier after the aforesaid step described under (2). As the coating technique, it is possible to employ the extrusion coating technique, the curtain coating technique, the casting technique, the screen printing technique, the spin coating technique, the spray coating technique, the slide beads coating technique, the slit and spin technique, the slit coating technique, the die coating technique, the dip coating technique, the knife coating technique, the blade coating technique, the flow coating technique, the roll coating technique, the wire bar boating technique, the transfer printing technique, or the like. With the arbitrary coating technique, the substance that contains the Group-15 or Group-16 atom, which has the metal coordinating capability, coordinates with the metal ions and is thereby fixed.

With the process for producing a carrier in accordance with the present invention, the carrier is produced by the aforesaid steps described under (1), (2), and (3). By way of example, the carrier having been prepared in the manner described above may be subjected to processing, wherein a composite body formed by two kinds of His-tag antibodies and one kind of an antigen is added and wherein the antibodies are taken out. In this manner, it is possible to produce the carrier applicable to the immune analysis technique utilizing the antigen-antibody reaction referred to as the sandwich technique. Also, with the processing, wherein a fluorescent label is added to the His-tag antibody, it is possible to produce the carrier for a test body analysis utilizing fluorescence resonance energy transfer.

(4) Application of the Process for Producing a Carrier in Accordance with the Present Invention The process for producing a carrier in accordance with the present invention is capable of being applied to a biosensor or a bioreactor. (Reference may be made to, for example, "Bioreactor Technology," 1988, CMC K.K.; and "Biochip and Biosensor," 2006, Kyoritsu Shuppan K.K.) The term "bioreactor" as used herein means the reactor, in which a biochemical reaction caused to occur by a bio-catalyst, such as an enzyme, a bacterium, a cell, or an organelle, is utilized for the production of a useful substance, the generation of energy, the decomposition of an environmental pollution substance, and the like. The term "biosensor" as used herein is interpreted in the broadest sense and means the sensor, in which an interaction between biomolecules is converted into a signal, such as an electric signal, and an objective substance is thereby analyzed and detected. The application of the process for producing a carrier in accordance with the present invention to the biosensor and the bioreactor will be described hereinbelow.

(4-1) Application to Bioreactor

In the cases of a bioreactor capable of performing the formation of a useful substance, the reaction, or the like, by use of an insoluble carrier, to which an enzyme has been fixed (as described in, for example, Japanese Utility Model Publication No. 4(1992)-18398 or 4(1992)-18399), as the insoluble carrier, it is possible to apply the carrier produced in accordance with the present invention, for example, the carrier comprising: (i) a carrier (e.g., a porous material, such as a ceramic material or a polysulfone material), (ii) a polymeric film, which has been bound on the surface of the carrier, (iii) a ligand, which has been bound with the polymeric film, (iv) a metal ion, which has been fixed to the ligand, and (v) an enzyme, which has been fixed to the metal ion.

(4-2) Application to Biosensor

An ordinary biosensor is constituted of a receptor site, which recognizes a chemical substance to be detected, and a transducer site, which transduces a physical change or a chemical change, which arises at the receptor site, into an electric signal. An organism contains various combinations of substances, which have affinity with each other, such as a combination of an enzyme and a substrate, a combination of an enzyme and a coenzyme, a combination of an antigen and an antibody, and a combination of a hormone and a receptor. The biosensor utilizes the principle such that one of the substances, which have the affinity with each other, is fixed to a carrier and utilized as a molecule recognizing substance, and such that the other substance is measured selectively.

For example, a surface plasmon resonance biosensor is constituted of a member containing a section, which transmits and reflects light having been irradiated from the sensor, and a member containing a section, which fixes a physiologically active substance. The carrier produced in accordance with the present invention is capable of being employed as the member containing the section, which fixes the physiologically active substance.

The surface plasmon resonance occurs due to the phenomenon such that an intensity of monochromatic light, which has been reflected from an interface between an optically transparent substance, such as glass, and a thin metal film layer, depends upon a refractive index of a sample located on the light radiating-out side of the thin metal film layer. Therefore, the sample is capable of being analyzed in accordance with the results of measurement of the intensity of the monochromatic light, which has been reflected from the interface described above.

As a surface plasmon analysis apparatus for analyzing characteristics of a substance, which is to be analyzed, by the utilization of the phenomenon, in which the surface plasmon is excited by a light wave, there may be mentioned an apparatus utilizing a system referred to as the Kretschmann arrangement. (The surface plasmon analysis apparatus utilizing the system referred to as the Kretschmann arrangement is described in, for example, Japanese Unexamined Patent Publication No. 6(1994)-167443.) Basically, the surface plasmon analysis apparatus utilizing the system referred to as the Kretschmann arrangement comprises: (i) a dielectric block having, for example, a prism-like shape, (ii) a metal film, which is formed on one surface of the dielectric block, and which is to be brought into contact with a substance to be analyzed, such as a liquid sample, (iii) a light source for producing a light beam, (iv) an optical system for irradiating the light beam to the dielectric block at various different incidence angles such that a total reflection condition may be obtained at an interface between the dielectric block and the metal film, and (v) photo detecting means for detecting the intensity of the light beam, which has been totally reflected from the interface described above, and thereby detecting the state of surface plasmon resonance, i.e. the state of attenuated total reflection.

As a similar analysis apparatus utilizing the attenuated total reflection (ATR), a leaky mode analysis apparatus has heretofore been known. The leaky mode analysis apparatus is described in, for example, "Bunko Kenkyu" (Spectrum Research), Vol. 47, No. 1, pp. 21-23 and 26-27, 1998.) Basically, the leaky mode analysis apparatus comprises: (i) a dielectric block having, for example, a prism-like shape, (ii) a cladding layer, which is formed on one surface of the dielectric block, (iii) an optical waveguide layer, which is formed on the cladding layer, and which is to be brought into contact with a liquid sample, (iv) a light source for producing a light beam, (v) an optical system for irradiating the light beam to the dielectric block at various different incidence angles such that a total reflection condition may be obtained at an interface between the dielectric block and the cladding layer, and (vi) a photo detecting means for detecting the intensity of the light beam, which has been totally reflected from the interface described above, and thereby detecting the state of excitation of a guided mode, i.e. the state of attenuated total reflection.

The constitution of the biosensor of the type described above is described in, for example, Japanese Patent Publication No. 6(1994)-27703, page 4, line 48 to page 14, line 15, and FIGS. 1 to 8; and U.S. Pat. No. 6,829,073, column 6, line 31 to column 7, line 47, and FIGS. 9A and 9B.

For example, in one aspect, a structure may be formed, wherein a waveguide layer, in which a thin layer is planar, is located on a base material (e.g., Pyrex glass (trade name)). The waveguide layer and the base material together form the so-called waveguide body. The waveguide layer may be constituted of a laminate of a plurality of layers, such as oxide layers (e.g., $SiO_2$, $SnO_2$, $Ta_2O_5$, $TiO_2$, $TiO_2$—$SiO_2$, $HfO_2$, $ZrO_2$, $Al_2O_3$, $Si_3N_4$, HfON, SiON, scandium oxide, and mixtures of the above-enumerated oxides) and plastic layers (e.g., a polystyrene, a polyethylene, and a polycarbonate). In order for a light beam to propagate in the waveguide layer through the total reflection, it is necessary that the refractive index of the waveguide layer is larger than the refractive index of the adjacent medium (such as the base material or the additional layer, which will be described later). A diffraction grating is located in the waveguide layer surface or the waveguide volume, which stands facing the base material or the substance to be analyzed. The diffraction grating is capable of being formed in the carrier by use of an embossing technique, a holography technique, or one of other techniques. Thereafter, a thin waveguide film having a higher refractive index is formed to cover the top surface of the diffraction grating. The diffraction grating has the function for converging the light beam impinging upon the waveguide layer, the function for radiating out the mode which is already being guided in the waveguide layer, and the function for transmitting a part of the mode to the travel direction and reflecting a part of the mode. The waveguide layer is set such that the grating region is covered by the additional layer. When necessary, the additional layer may be constituted of a multi-layer film. The additional layer may be imparted with the function for enabling selective detection of a substance contained in the substance to be analyzed. As a preferable example, a layer having the detecting function may be formed on the outermost surface of the additional layer. As the layer having the detecting function described above, it is possible to utilize the layer capable of fixing the physiologically active substance.

In a different aspect, an array of diffraction grating waveguides may be incorporated in a well of a micro-plate. (Reference may be made to, for example, PCT Japanese Publication No. 2007-501432.) Specifically, in cases where the diffraction grating waveguides are located in an array pattern at the well bottom surface of the micro-plate, it is possible to perform screening of drugs or chemical substances with a high throughput.

In cases where the diffraction grating waveguides are utilized, such that the detection of the physiologically active substance on the top layer (the detecting region) of the diffraction grating waveguides may be capable of being performed, an incident light beam and a reflected light beam are detected, and an alteration of the refraction characteristics is detected. For such purposes, at least one light source (e.g., a laser or a diode) and at least one detector (e.g., a spectrometer, a CCD camera, or one of other photodetectors) are capable of being utilized. As the technique for measuring the alteration of the refractive index, one of two different operation modes, i.e. a spectrometric technique and an angle technique, may be utilized. With the spectrometric technique, a broad-band beam is sent as the incident light beam to the diffraction grating waveguide, and the reflected light beam is collected and measured with, for example, a spectrometer. With the observation of a spectrum position of a resonance wavelength (peak), it is possible to measure the alteration of the refractive index, i.e. the binding, at the surface of the diffraction grading waveguide or at the position in the vicinity of the surface of the diffraction grading waveguide. With the angle technique, a light beam nominally having a single wavelength is converged so as to form a certain range of irradiation angle and is irradiated to the diffraction grating waveguide. The resulting reflected light is measured with a CCD camera or one of other photodetectors. With the measurement of the position of a resonance angle reflected by the diffraction grating waveguide, it is possible to measure the alteration of the refractive index, i.e. the binding, at the surface of the diffraction grading waveguide or at the position in the vicinity of the surface of the diffraction grating waveguide.

The process for producing a carrier in accordance with the present invention will further be illustrated by the following non-limitative examples.

EXAMPLES

Example 1

Preparation of Carrier Imparted with Carboxyl Group (Formation of Self-Assembled Monolayer)

After Sensor Chip Au (supplied by Biacore) constituted of a sensor chip, on which only a gold film had been formed, was subjected to UV ozone processing for 12 minutes, a solution, which contained 10 μmol of 6-aminohexanethiol (supplied by Aldrich) dissolved in 8 ml of ethanol and 2 ml of ultra pure water, was allowed to undergo reaction with the gold film at a temperature of 40° C. for one hour. An amino group was thus formed on the gold film. The sensor chip was then washed one time with ethanol and was thereafter washed one time with ultra pure water.

(Activating Esterification of CMD)

A CMD solution was prepared with processing wherein CMD (molecular weight: 1,000,000, supplied by Meito Sangyo Co., Ltd.) was dissolved in ultra pure water so as to have a concentration of 0.5% by weight. Thereafter, a mixed solution, which contained 0.4M of EDC (i.e., 1-(3-dimethylaminopropyl)-3-ethylcarbodiimide) and 0.1M of NHS (i.e., N-hydroxysuccinimide), was added to the CMD solution. The mixed solution was added in a stoichiometric quantity having been calculated such that, in cases where the entire quantity had undergone the reaction, 2% of the carboxyl group might be activated. The resulting reaction mixture was stirred at the room temperature for five minutes.

(Preparation of CMD Film)

The CMD solution having been subjected to the activating esterification was added little by little onto the gold film, on which the amino group had been formed. The CMD solution was then removed after a period of time of 30 seconds. In this manner, a thin film of carboxymethyl dextran having been subjected to the activating esterification was formed on the carrier having the amino group. After being allowed to undergo the reaction at the room temperature for one hour, the thin film was washed one time with 0.1N NaOH and was then washed one time with ultra pure water.

(Binding of Complex)

A solution was prepared by the addition of 1 mmol of EDC and 0.2 mmol of NHS to 1 ml of DMSO, and 50 μl of the thus prepared solution was added onto the CMD film. The solution was then allowed to undergo the reaction at the room temperature for 30 minutes. After the solution was removed, washing with DMSO was performed one time. Also, a solution, which had been prepared previously by mixing 0.1 mmol of AB-NTA (supplied by Dojin Kagaku K.K.), 0.04 mmol of $CuCl_2$ (supplied by Wako Pure Chemical Industries, Ltd.), 60 μl of DBU (diazabicycloundecene, supplied by Tokyo Chemical Industry Co., Ltd.), and 0.94 ml of DMSO, and allowing the resulting mixture to stand for 10 minutes, was allowed to undergo the reaction for two hours. In this manner, a metal complex of AB-NTA and Cu was bound on the CMD film. The solution was removed, and dip washing with ultra pure water was performed for 30 minutes.

(Preparation of Close Chelate Modified Film and Fixation of Protein)

The sample having been prepared was set on a surface plasmon resonance apparatus (Biacore3000, supplied by Biacore). After an SPR HEPES buffer (20 mM HEPES-HCl, 150 mM NaCl, pH7.4) was stabilized at a flow rate of 10 μl/min, 10 μl of an aqueous 1 mM $CuCl_2$ solution was added. Thereafter, washing with 20 μl of an HBS-N buffer was performed one time. Thereafter, 30 μl of an aqueous 1.8 μM His6-Ubiquitin solution was added. In this manner, a chip for surface plasmon resonance analysis was prepared.

Example 2

At the stage of the binding of the complex in Example 1, in lieu of 0.04 mmol of $CuCl_2$, 0.04 mmol of $InCl_3$ (supplied by Wako Pure Chemical Industries, Ltd.) was used. The resulting mixture was allowed to stand for one hour and was allowed to undergo the reaction for two hours. In this manner, a metal complex of AB-NTA and In was bound on the CMD film. The solution was removed, and washing with 0.5M EDTA having a pH value of pH8 (supplied by Wako Pure Chemical Industries, Ltd.) was performed for one minute in Biacore3000. Also, at the stage of the fixation of the protein, in lieu of 30 μl of the aqueous 1.8 μM His6-Ubiquitin solution being added, 10 μl of 5 μM HHHHHH peptide (where H represents histidine, HHHHHH represents a linkage of six pieces of histidine, supplied by NeoMPS Co.) was added. The other procedure was performed in the same manner at that in Example 1, and a chip for surface plasmon resonance analysis was prepared.

Example 3

At the stage of the binding of the complex in Example 1, in lieu of 0.1 mmol of AB-NTA and 0.04 mmol of $CuCl_2$ being used, 0.05 mmol of AB-NTA and 0.02 mmol of $HfCl_4$ (supplied by Wako Pure Chemical Industries, Ltd.) were used. After the resulting mixture was heated to 40° C., the resulting mixture was allowed to stand for one hour and was allowed to undergo the reaction for two hours. In this manner, a metal complex of AB-NTA and Hf was bound on the CMD film. The solution was removed, and washing with 100 mM NaOH (supplied by Wako Pure Chemical Industries, Ltd.) was performed for one minute in Biacore3000. The other procedure was performed in the same manner at that in Example 2, and a chip for surface plasmon resonance analysis was prepared.

Example 4

At the stage of the fixation of the protein in Example 1, in lieu of 30 μl of the aqueous 1.8 μM His6-Ubiquitin solution being added, 10 μl of 5 μM HSHSHSHSHSHSHSHSHSHS peptide (where H represents histidine, S represents serine, HSHSHSHSHSHSHSHSHSHS represents a linkage of ten HS bonds of histidine and serine, supplied by Operon) was added. The other procedure was performed in the same manner at that in Example 1, and a chip for surface plasmon resonance analysis was prepared.

Example 5

At the stage of the fixation of the protein in Example 1, in lieu of 30 μl of the aqueous 1.8 μM His6-Ubiquitin solution being added, 10 μl of 5 μM HKHKHKHKHKHK peptide (where H represents histidine, K represents lysine, HKHKHKHKHKHK represents a linkage of six HK bonds of histidine and lysine, supplied by Operon) was added. The other procedure was performed in the same manner at that in Example 1, and a chip for surface plasmon resonance analysis was prepared.

Example 6

At the stage of the fixation of the protein in Example 1, in lieu of 30 μl of the aqueous 1.8 μM His6-Ubiquitin solution being added, 10 μl of 5 μM HCHCHCHCHCHC peptide (where H represents histidine, C represents cysteine, HCHCHCHCHCHC represents a linkage of six HC bonds of histidine and cysteine, supplied by Operon) was added. The other procedure was performed in the same manner at that in Example 1, and a chip for surface plasmon resonance analysis was prepared.

Comparative Example 1

In Example 1, the complex was not bound. Also, a solution containing 0.1 mmol of AB-NTA (supplied by Dojin Kagaku K.K.) in 60 μl of DBU (diazabicycloundecene) and 0.94 ml of DMSO was used. The other procedure was performed in the same manner at that in Example 1, and a chip for surface plasmon resonance analysis was prepared.

Comparative Example 2

At the stage of the fixation of the protein, in lieu of 30 μl of the aqueous 1.8 μM His6-Ubiquitin solution being added, 5 μM HHHHHH peptide (supplied by NeoMPS Co.) was added. The other procedure was performed in the same manner at that in Comparative Example 1, and a chip for surface plasmon resonance analysis was prepared.

(Measurement of Protein Fixation Rate)

As for each of the chips for surface plasmon resonance analysis having been prepared in Example 1 and Comparative Example 1, alteration of a protein dissociation quantity with the passage of time at the stage immediately after the protein fixation was performed and at the stage after the SPR HEPES buffer was flown continuously for 48 hours was measured by use of Biacore3000. The results shown in Table 1 below were obtained. Table 1 shows the protein fixation quantity in Example 1 having been calculated with the protein fixation quantity after 48 hours in Comparative Example 1 being taken as 1.

Figure 2:
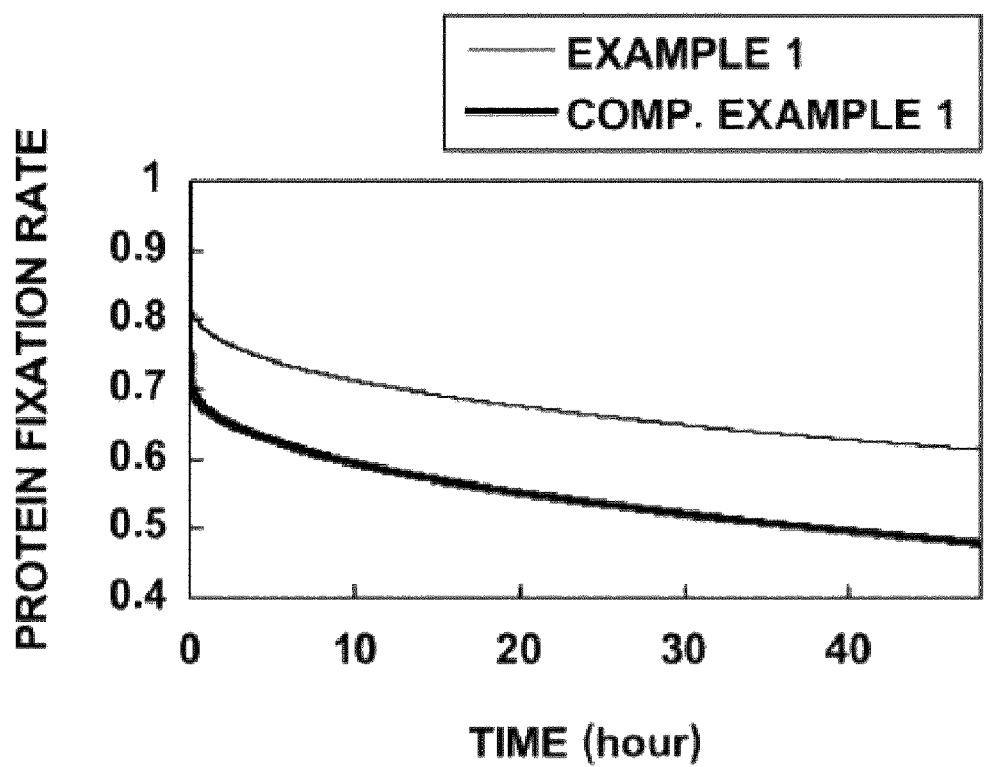
FIG. 2 is a graph showing alterations of a protein fixation rate with the passage of time in Example 1 in accordance with the present invention and in Comparative Example 1.

FIG. 2 is a graph showing alterations of a protein fixation quantity (a protein fixation rate) with the passage of time of 48 hours with the protein fixation quantity at the stage immediately after the protein fixation being taken as 1, which alterations were found for the chips for surface plasmon resonance analysis having been prepared in Example 1 and Comparative Example 1.

TABLE 1

| | Protein fixation quantity after 48 hours |
|---|---|
| Example 1 | 1.28 |
| Comp. Example 1 | 1 |

In Comparative Example 1, instead of the complex being bound on the carrier, AB-NTA was bound with the carrier, and thereafter $CuCl_2$ was subjected to the reaction. In such cases, since adjacent pieces of NTA were not close to one another, the protein was not easily supported at multiple points. Therefore, as clear from Table 1 and FIG. 2, the protein fixation rate, i.e. the protein support capability after 48 hours, was low. In Example 1, after the complex had been bound on the carrier, the metal ion was added even further, and the new complex was formed. In such cases, since adjacent pieces of NTA were close to one another, the protein was supported at multiple points, and the protein fixation rate was high. In cases where the protein fixation rate was high, the interaction with the sample substance was capable of being detected reliably, and the detection sensitivity was capable of being kept high.

(Measurement of Peptide Fixation Rate)

As for each of the chips for surface plasmon resonance analysis having been prepared in Examples 2 to 6 and Comparative Example 2, alteration of a peptide dissociation quantity with the passage of time at the stage immediately after the peptide fixation was performed and at the stage after the SPR HEPES buffer was flown continuously for 10 hours was measured by use of Biacore3000. The results shown in Table 2 below were obtained. Table 2 shows the peptide fixation quantity in each of Examples 2 to 6 having been calculated with the peptide fixation quantity after 10 hours in Comparative Example 2 being taken as 1.

TABLE 2

|  | Peptide fixation quantity after 10 hours |
| --- | --- |
| Example 2 | 1.22 |
| Example 3 | 1.27 |
| Example 4 | 1.59 |
| Example 5 | 1.54 |
| Example 6 | 1.60 |
| Comp. Example 2 | 1 |

As clear from Table 2, the peptide fixation quantity in each of Examples 2 to 6 was larger than the peptide fixation quantity in Comparative Example 2. It was thus found that, in cases where the metal complex of the In ion or the Hf ion, which did not directly participated in the peptide fixation, was fixed, the useful effects were obtained in the fixation of the histidine residue. Also, it was found that it was possible to fix histidine, lysine, or cysteine containing the Group-15 or Group-16 atom.

What is claimed is:

1. A process for producing a carrier, comprising the steps of:
   (1) binding a complex, which has been formed by at least two pieces of a ligand and a first metal ion, with a carrier,
   (2) adding a second metal ion onto the carrier, a new complex being thereby formed, and
   (3) fixing a substance that contains a Group-15 or Group-16 atom, which has metal coordinating capability, to the first metal ion and the second metal ion,
   the steps (1), (2), and (3) being performed in this order.

2. A process as defined in claim 1 wherein a quantity of the second metal ion added in the step (2) is set at a value which cleaves approximately all of the complex having been bound to the carrier in the step (1).

3. A process as defined in claim 2 wherein the ligand is a nitrilotriacetic acid derivative.

4. A process as defined in claim 3 wherein the first metal ion, which is employed in the step (1), and/or the second metal ion, which is employed in the step (2), is a transition metal ion.

5. A process as defined in claim 4 wherein the transition metal ion, which is employed in the step (2), is selected from the group consisting of a nickel ion, a copper ion, and a cobalt ion.

6. A process as defined in claim 3 wherein the substance that contains the Group-15 or Group-16 atom is a substance having at least two heterocyclic rings each of which contains the Group-15 or Group-16 atom.

7. A process as defined in claim 4 wherein the substance that contains the Group-15 or Group-16 atom is a substance having at least two heterocyclic rings each of which contains the Group-15 or Group-16 atom.

8. A process as defined in claim 5 wherein the substance that contains the Group-15 or Group-16 atom is a substance having at least two heterocyclic rings each of which contains the Group-15 or Group-16 atom.

9. A process as defined in claim 6 wherein the substance having at least two heterocyclic rings is a physiologically active substance having at least two heterocyclic rings each of which contains the Group-15 or Group-16 atom.

10. A process as defined in claim 7 wherein the substance having at least two heterocyclic rings is a physiologically active substance having at least two heterocyclic rings each of which contains the Group-15 or Group-16 atom.

11. A process as defined in claim 8 wherein the substance having at least two heterocyclic rings is a physiologically active substance having at least two heterocyclic rings each of which contains the Group-15 or Group-16 atom.

12. A process as defined in claim 9 wherein the physiologically active substance is a physiologically active substance having at least two imidazole groups.

13. A process as defined in claim 10 wherein the physiologically active substance is a physiologically active substance having at least two imidazole groups.

14. A process as defined in claim 11 wherein the physiologically active substance is a physiologically active substance having at least two imidazole groups.

15. A process as defined in claim 2 wherein a fixation quantity of the complex having been bound with the carrier in the step (1) falls within the range of $1\times10^{-12}$ g/mm$^3$ to $1\times10^{-3}$ g/mm$^3$.

16. A process as defined in claim 3 wherein a fixation quantity of the complex having been bound with the carrier in the step (1) falls within the range of $1\times10^{-12}$ g/mm$^3$ to $1\times10^{-3}$ g/mm$^3$.

17. A process as defined in claim 4 wherein a fixation quantity of the complex having been bound with the carrier in the step (1) falls within the range of $1\times10^{-12}$ g/mm$^3$ to $1\times10^{-3}$ g/mm$^3$.

18. A process as defined in claim 5 wherein a fixation quantity of the complex having been bound with the carrier in the step (1) falls within the range of $1\times10^{-12}$ g/mm$^3$ to $1\times10^{-3}$ g/mm$^3$.

19. A process as defined in claim 1 wherein the carrier is utilized as a carrier for a bioreactor or a biosensor.

20. A process as defined in claim 1 wherein the carrier is utilized as a carrier for surface plasmon resonance analysis.

* * * * *